United States Patent [19]

Martini

[11] 4,140,699

[45] Feb. 20, 1979

[54] PROCESS FOR PREPARING PERFLUORINATED VINYL ETHERS

[75] Inventor: Thomas Martini, Neuenhain, Fed. Rep. of Germany

[73] Assignee: Hoechst Aktiengesellschaft, Frankfurt (Main), Fed. Rep. of Germany

[21] Appl. No.: 743,958

[22] Filed: Nov. 22, 1976

Related U.S. Application Data

[62] Division of Ser. No. 677,513, Apr. 16, 1976, Pat. No. 4,013,689.

[30] Foreign Application Priority Data

Apr. 19, 1975 [DE] Fed. Rep. of Germany ....... 2517357

[51] Int. Cl.$^2$ .......................................... C07D 319/10
[52] U.S. Cl. ........................... 260/340.6; 260/33.2 R; 260/45.8 A
[58] Field of Search ..................................... 260/340.6

[56] References Cited

FOREIGN PATENT DOCUMENTS 1162829 2/1964 Fed. Rep. of Germany.

Primary Examiner—Ethel G. Love
Attorney, Agent, or Firm—Curtis, Morris & Safford

[57] ABSTRACT

Perfluorinated vinyl ethers are prepared by reacting a fluorinated carboxylic acid fluoride with hexafluoropropylene epoxide in the presence of a catalyst and thereafter pyrolyzing the carboxylic acid fluoride containing ether linkages, optionally after having converted it into a salt of a monovalent metal.

5 Claims, No Drawings

PROCESS FOR PREPARING PERFLUORINATED VINYL ETHERS

This is a division, of application Ser. No. 677,513, filed Apr. 16, 1976, now U.S. Pat. No. 4,013,689.

Perfluorinated compounds are distinguished by their low chemical reactivity and their thermal resistance. For this reason representatives of this type are used as heat transferring agents, dielectric agents, lubricants and solvents.

German Patent No. 1,162,829 discloses a process for preparing perfluorinated vinyl ethers, which comprises reacting a fluorinated carboxylic acid fluoride with hexafluoropropylene epoxide in the presence of a catalyst and thereafter pyrolyzing the carboxylic acid fluoride containing ether linkages optionally after having converted it into a salt of a monovalent metal.

It has now been found that also acid fluorides of the formula

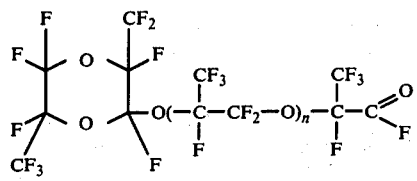

wherein n is 1 or 0,
may be used as carboxylic acid fluorides containing ether linkages for this purpose.

The present invention consequently provides a process for preparing perfluorinated vinyl ethers of the formula

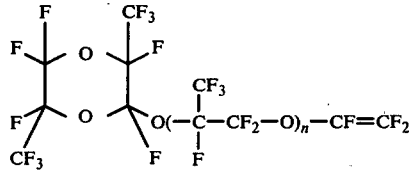

wherein n is 0 or 1,
which comprises hydrolyzing an acid fluoride of the formula

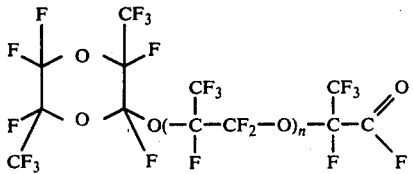

to yield the corresponding perfluorocarboxylic acid, neutralizing the acid obtained and heating the salt of the carboxylic acid obtained at neutralization to a temperature above 150° C.

The present invention moreover provides a process for the preparation of perfluorinated vinyl ethers of formula I, which comprises heating an acid fluoride of the formula

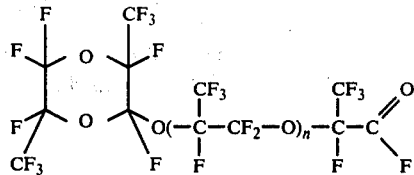

wherein n is 1 or 0,
to temperature in the range of from 200 to 400° C.; the pyrolysis of the acid fluoride is advantageously performed at a temperature of from 300° to 350° C.

The pyrolysis of the acid fluoride may be facilitated by catalysis on metal oxides according to the process of U.S. Pat. No. 3,321,532.

The present invention finally provides the novel perfluoronated vinyl ethers of the formula

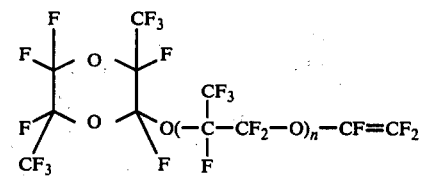

wherein n is 1 or 0.

Transferring of the acid fluoride of formula II into a salt of a monovalent metal may be performed without difficulty by one skilled in the art. The hydrogenolysis of the acid fluoride is carried advantageously with water containing about stoichiometrical quantities of a basic substance in a dissolved state. It is also possible to hydrolyze with pure water and to neutralize subsequently the acid solution containing fluorides with basic substances. The salts are isolated thereafter, for example by evaporation of the aqueous solution. Suitable bases are especially compounds of alcaline metals, for example hydroxydes or carbonates. The sodium and potassium salts are used preferably because of their quick and smooth decomposition. A removal of the inorganic fluoride formed simultaneously is not required generally.

Prior to its decomposition the carboxylic acid salt obtained must be carefully dried. The decomposition is performed in a closed apparatus, for example in a rotation evaporator, by heating to temperatures above 150° C., generally of from 160 to 300° C., preferably of from 190 to 230° C., most suitably in vacuo, because the cleavage products in this case only remain for a short time in the pyrolysis zone. It is operated preferably under a pressure of less than 10 torrs, especially of from 0.1 to 5 torrs. The vinyl ether formed of formula I is distilled off and may be collected in cooled receivers and then be further purified, preferably by fractionated distillation.

Decomposition may also be performed under atmospheric pressure, whereby by-products may easily be formed, for example products containing hydrogen, if the starting product is not absolutely dry.

The vinyl ethers obtained are colorless liquids and may be used in a wide field of application as intermediates. They may be converted into saturated fluorinated ethers, for example by addition of elementary fluorine. The perfluoroethoxy derivatives obtained are chemically inert to a large extent. Perfluoro-[3.6-dimethyl-2-ethoxydioxane-1.4] for example, may be used as lubricant, sealing liquid, heat transferring agent, insulating liquid or hydraulic liquid. The vinyl ethers may also be used as monomers for copolymers.

The vinyl ethers may especially react with perfluorinated acid fluorides according to the equation

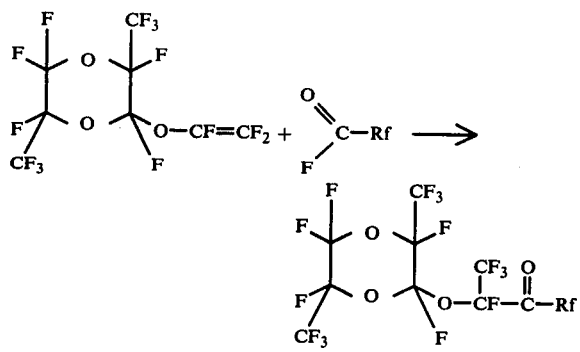

wherein Rf means a perfluorinated alkyl or polyoxalkyl radical, yielding saturated perfluorinated carbonyl ethers. This possibility is especially important for perfluorinated polyether carboxylic acid fluorides formed during the oligomerization or polymerization of hexafluoropropene oxide, because the reactive terminal groups of these polymers are masked thereby. In this process there are obtained thermally and chemically stable products having a molar weight increased by the molar weight of the vinyl ether in comparison with that of the starting compound. In ths way the complicated elimination of the COF groups by means of elementary fluorine according to U.S. Pat. No. 3,242,218 may be dispensed with. The products obtained when using the perfluorinated vinyl ethers according to the invention are nevertheless resistant towards and oxidants. The starting products of the process according to the invention (acid fluorides) are readily aceesible as there is only obtained a small variety of oligomers during their preparation from hexafluoropropene oxide, oligomers only differing from one another by the number of the added units of hexafluoropropene oxide. For this reason it is possible to prepare homogeneous vinyl ethers with very good yields (calculated on hexafluoropropene oxide).

The following examples illustrate the invention:

EXAMPLE 1

Perfluoro-3,6-dimethyl-1,4-dioxanyl-2-vinyl ethers 2800 g of a mixture of hexafluoropropene oxide and hexafluoropropene (in weight ratio of 65:35) were introduced into a solution of 600 ml of diethylene glycol dimethyl ether and 600 g of $PO[N(CH_3)_2]_3$, in a three neck flask provided with an intensive condenser, a stirrer and a thermometer for low temperatures, at a temperature from $-40$ to $-30°$ C. while stirring continuously, at a rate of 40 l/hour (measured under normal conditions).

Stirring was then continued for 5 hours at the above mentioned temperature. Hexafluoropropene and the excess of epoxide then removed by heating slowly to 0° C. and the two phase mixture was separated in a separating funnel. The lower phase (1742 g) was washed with 600 ml of acetonitrile and yielded 1554 g of product mixture. 1142 g of a substance boiling at a temperature of from 115 to 118° C. and 194 g of a second fraction boiling at a temperature of from 118 to 170° C. were obtained from the latter mixture by fractionated distillation. Elementary, infra-red and a NMR-spectroscopic analyses revealed the formula

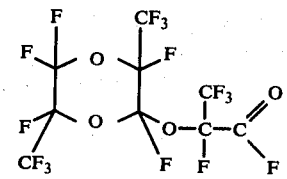

for the first fraction, representing the perfluoro-[α-3,6-dimethyl-1,4-dioxanyl-2-]-propionic acid fluoride, hitherto unknown.

794 g of this substance (1.67 mole) were then added dropwise to 160 ml of water while cooling with ice and stirring. Then the reaction mixture was neutralized with an aqueous 20 percent by weight KOH solution and concentrated in a rotation vaporator. The material thus predried was kept on a drying sheet in a vacuum oven for 24 hours at a temperature of 100° C. under a pressure of 300 torrs, it was ground to fine particles and heated again for the same period to 100° C. under a pressure of 0.1 torr.

The dry material obtained was heated in a 2 liter round-bottomed flask coupled with two refrigerating traps, under a vacuum of from 5 to 1 torr for a period of 30 hours at a temperature of from 200 to 225° C. The collected pyrolysate (628 g) was distilled by fractionation.

After a first fraction of 8 g (boiling point of from 97 to 103° C.), 584 g (85.2% of the theory) of perfluorinated-3,6-dimethyl-1,4-dioxanyl-2-vinyl ether having a boiling point of from 103 to 106° C. were obtained. A residue of 32 g did not distill.

$C_8F_{14}O_3$
MG 410

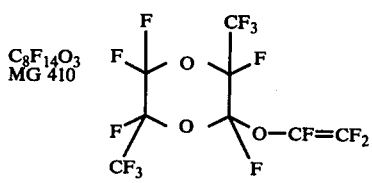

The infra-red and $^{19}F$-NMR spectra back this structure. There appears a strong band at 9.65 μ in the infrared spectrum.

Analysis

Calculated: C 23.4%; F 64.9 %.

Found: C 23.6%; F 65.2%.

EXAMPLE 2

Perfluoro-[α-(3,6-dimethyl-1,4-dioxanyl-2-oxy-propyl)-vinyl ethers]

From the second fraction formed during the preparation of perfluoro-[α-3,6-dimethyl-1,4-dioxanyl-2-oxy]-propionic acid fluoride according to Example 1, 67% by weight of a compound having a boiling range of from 160 to 164° C. could be obtained by a second fractionated distillation. The compound has the structure

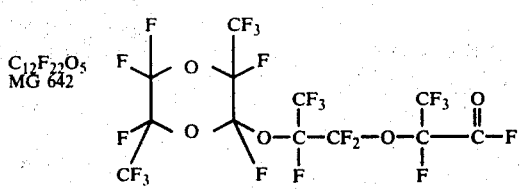

according to the elementary, infra-red and NMR spectroscopic analyses, being perfluoro-[α-(3,6-dimethyl-1,4-dioxanyl-2-oxy-propoxy)]propionic acid fluoride.

Analysis
Calculated: C 22.4%; F 65.2%.
Found: C 22.3%; F 65.0%.

623 g (0.97 mole) of said acid fluoride were given dropwise to 100 ml of water while cooling with ice. Then the mixture obtained was neutralized with aqueous 10percent by weight KOH solution and concentrated in the rotation evaporator. The predried material was then kept firstly for 15 hours at a temperature of 100° C. under a pressure of 300 torrs and then further dried for 62 hours at a temperature of 100° C. under a pressure of 0.1 torr. Then it was heated to 200° C. under a pressure of from 5 to 0.1 torrs for 24 hours. The pyrolysis was performed according to Example 1. The distillation of the pyrolysate yielded 346 g (61.9% of the theory) of a vinyl ether having a boiling point of from 151 to 154° C. and a formula

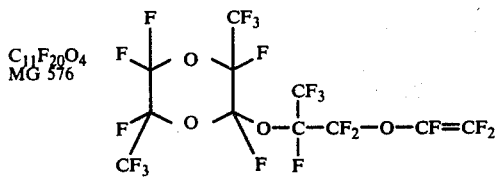

according to the analyses by NMR, IR and mass-spectrometry and to the elementary analysis.

Analysis: Calculated: C 22.9%; F 65.9%. Found: C 22.8%; F 65.5%.

EXAMPLE 3

Saturation of the terminal group of a hexafluoropropene oxide polymer 100 g of a hexafluoropropene oxide polymer having a boiling point of from 85 to 107° C./1 mm, an average molecular weight of about 1100 and the formula

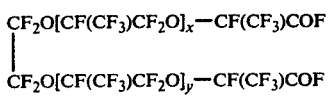

wherein x + y = 4 (average value), was dissolved in 70 ml of diglyme. 30 g of CsF and 200 g of perfluoro-3,6-dimethyl-1,4-dioxanyl-2-vinyl ether were added and the mixture was stirred for 55 hours at 60° C. The heavy phase was separated and distilled. 120 g of a colorless liquid were obtained as main fraction having a boiling point of from 93 to 138° C. under 0.09 torr, in which acid fluoride groups (5.32$_{82}$) could not be detected by IR spectroscopic analysis, whereas a band probably belonging to the β-carbonyl ether group (C=O), appeared at 5.62μ.

The average molecular weight (about 1900) as well as the C/F analyses of the termal product did agree with the calculated composition $C_{36}F_{66}O_{14}$.

What is claimed is:

1. A process for preparing a perfluorinated vinyl ether of the general formula

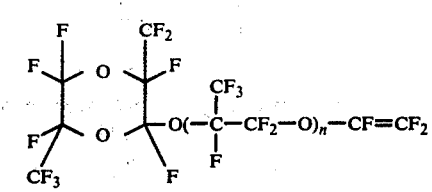

which comprises hydrolyzing an acid fluoride of the formula

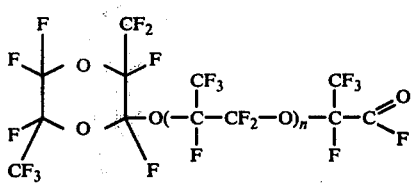

wherein n is 0 or 1,
to form the corresponding perfluorinated carboxylic acid, thereafter neutralizing the acid and heating the resulting salt of the carboxylic acid to a temperature of 160° to 300° C. at a pressure of less than 10 torrs.

2. Process as claimed in claim 1, which comprises heating the carboxylic acid salt to a temperature of from 190 to 230° C.

3. Process as claimed in claim 1, which comprises performing the heating of the carboxylic acid salt under reduced pressure.

4. A process for preparing a perfluorinated vinyl ether of the general formula

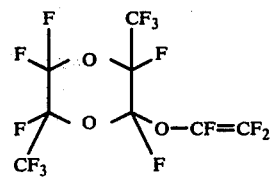

which comprises hydrolyzing an acid fluoride of the formula

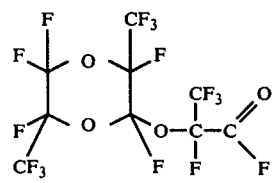

to form the corresponding perfluorinated carboxylic acid, thereafter neutralizing the acid and heating the resulting salt of the carboxylic acid to a temperature of 160° to 300° C. at a pressure of less tha 10 torrs.

5. A process for preparing a perfluorinated vinyl ether of the general formula which comprises hydrolyzing an acid fluoride of the formula
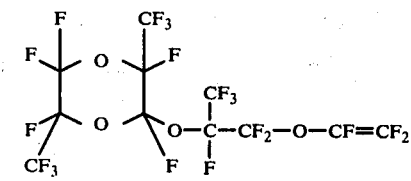
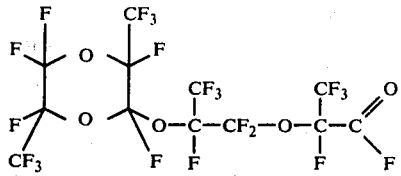
to form the corresponding perfluorinated carboxylic acid, thereafter neutralizing the acid and heating the resulting salt of the carboxylic acid to a temperature of 160° to 300° C. at a pressure of less than 10 torrs.
* * * * *